United States Patent
Qiu

(10) Patent No.: US 11,090,200 B2
(45) Date of Patent: Aug. 17, 2021

(54) DISPOSABLE NURSING DEVICE WITH URINE AND FECES BACK-LEAKAGE PREVENTION COLLECTION FUNCTION

(71) Applicant: JIANGSU ZHONGHENG PET ARTICLES JOINT-STOCK CO., LTD., Jiangsu (CN)

(72) Inventor: Bin Qiu, Jiangsu (CN)

(73) Assignee: JIANGSU ZHONGHENG PET ARTICLES JOINT-STOCK CO., LTD., Jiangsu (CN)

( * ) Notice: Subject to any disclaimer, the term of this patent is extended or adjusted under 35 U.S.C. 154(b) by 239 days.

(21) Appl. No.: 16/378,574

(22) Filed: Apr. 9, 2019

(65) Prior Publication Data

US 2020/0323706 A1 Oct. 15, 2020

(51) Int. Cl.
*A61F 13/495* (2006.01)
*A61F 13/58* (2006.01)
*A61F 13/49* (2006.01)

(52) U.S. Cl.
CPC ...... *A61F 13/495* (2013.01); *A61F 13/49058* (2013.01); *A61F 13/58* (2013.01); *A61F 2013/4951* (2013.01); *A61F 2013/4953* (2013.01)

(58) Field of Classification Search
CPC .. A61F 2013/55125; A61F 2013/55155; A61F 13/495; A61F 13/58; A61F 13/49058; A61F 2013/4951–4958; A61F 5/4401; A61F 5/445; A61F 2005/4402; A61F 2005/4408; A61F 2013/4953
See application file for complete search history.

(56) References Cited

U.S. PATENT DOCUMENTS

| 3,577,989 | A | * | 5/1971 | Anderson | A61F 5/4401 604/348 |
| 9,937,083 | B1 | * | 4/2018 | Neuenschwander | A61F 13/47272 |
| 2003/0050614 | A1 | * | 3/2003 | D'Acchioli | A61F 13/493 604/346 |
| 2004/0193130 | A1 | * | 9/2004 | Fima | A61F 13/495 604/385.01 |

FOREIGN PATENT DOCUMENTS

WO WO-2016122152 A1 * 8/2016 ............... A61F 5/44

* cited by examiner

*Primary Examiner* — Nicholas J Weiss
*Assistant Examiner* — Eric Rassavong
(74) *Attorney, Agent, or Firm* — JCIP Global Inc.

(57) ABSTRACT

A disposable nursing device with a urine and feces back-leakage prevention collection function includes a nursing pants body, a urine and feces collection bag and a catch tray. The nursing pants body is provided with a connecting port. The urine and feces collection bag is provided with an outer layer and an inner layer. The outer layer is a soft non-woven fabric, and the inner layer is a polymer absorption layer. A bottom portion of the urine and feces collection bag is closed, and a top portion of the urine and feces collection bag is provided with a bag opening. A urine and feces collection opening is arranged at a middle of the catch tray, and one side of the catch tray is connected with the bag opening of the urine and feces collection bag, and is connected with the connecting port on the nursing pants body.

8 Claims, 6 Drawing Sheets

DISPOSABLE NURSING DEVICE WITH URINE AND FECES BACK-LEAKAGE PREVENTION COLLECTION FUNCTION

BACKGROUND

Technical Field

The present invention relates to a device for collecting urine and feces of disabled elderly or patients, children and pets in medical equipment, and more particularly, to a disposable nursing device with a urine and feces back-leakage prevention collection function.

Description of Related Art

A paper diaper is mainly used by infants and adults, that is, the paper diaper is divided into an infant paper diaper and an adult paper diaper, which are both disposable products. The adult paper diaper is a disposable paper incontinence product and one of adult care products, and is the disposable diaper mainly suitable for incontinent adults. Most products are sheets when purchasing, and become pants when wearing. An adhesive tape is used to connect the sheet into a pair of pants. The adhesive tape also has the function of adjusting a waist size of the pants, so as to be suitable for different fat and thin bodies. Generally, the paper diaper is structurally divided into three layers from the inside to the outside, wherein an inner layer clings to the skin and is made of non-woven fabric; a middle layer is water-absorbing fluff pulp and is added with polymer water absorbing agent; and an outer layer is an impermeable plastic film.

However, the existing adult paper diaper also has various problems, such as weak back-leakage prevention property, difficulty in removal and replacement, large contact area with skin after urine and feces are defecated into the paper diaper, inconvenience for nursing personnel to handle, etc.

SUMMARY

The present invention is intended to provide a disposable medical nursing device with a urine and feces back-leakage prevention collection function, which is respectively used by males and females, and a back-leakage prevention hygroscopic detachable urine and feces collection structure is additionally arranged on a paper diaper, which is suitable for defecating and collecting urine and feces of the disabled elderly or incontinent patients, children and pets.

In order to achieve the object above, the present invention provides a disposable nursing device with a urine and feces back-leakage prevention collection function, wherein the device includes a nursing pants body, a urine and feces collection bag, and a catch tray; the nursing pants body is a paper diaper which can be opened and closed on left and right sides, and the nursing pants body is provided with a connecting port; the urine and feces collection bag is provided with an outer layer and an inner layer, the outer layer is a soft non-woven fabric, and the inner layer is a polymer absorption layer; a bottom portion of the urine and feces collection bag is closed, a top portion of the urine and feces collection bag is provided with a bag opening, and a bag body is a closed structure except at the bag opening; the bag opening of the urine and feces collection bag is connected with the connecting port on the nursing pants body through the catch tray; and a urine and feces collection opening is arranged at a middle of the catch tray, and one side of the catch tray is connected with the bag opening of the urine and feces collection bag, and is connected with the connecting port on the nursing pants body. The nursing pants are disposable sanitary articles after sterilization treatment.

According to the disposable nursing device with the urine and feces back-leakage prevention collection function above, the left and right sides of the nursing pants body are respectively provided with an opening penetrating from top to bottom, so that the nursing pants body can be unfolded into a plane; and surfaces of the nursing pants body on two sides of the openings are respectively provided with a corresponding adhesive tape. The adhesive tape is preferably in the form of an adhesive sheet or a hook and loop, and can be repeatedly opened and closed many times. An upper edge of the nursing pants body is provided with an elastic edge with elasticity.

According to the disposable nursing device with the urine and feces back-leakage prevention collection function above, the nursing pants body includes a male style and a female style, the nursing pants body of the male style is respectively provided with one connecting port at a front side and a rear side, which are a first connecting port and a second connecting port respectively, and the nursing pants body of the female style is provided with one connecting port at a rear side, which is the second connecting port; and the connecting port is a circular port corresponding to a defecation position of a human body, and an inner surface of the nursing pants body at an edge of the connecting port is provided with an adhesive strip.

According to the disposable nursing device with the urine and feces back-leakage prevention collection function above, an outer surface of the nursing pants body is a soft non-woven fabric, an inner surface of the nursing pants body is a polymer absorption layer, and the polymer absorption layer is an absorption layer compounded by polymer absorbent resin and fluff fiber. The soft non-woven fabric and the polymer absorption layer are integrated.

According to the disposable nursing device with the urine and feces back-leakage prevention collection function above, the polymer absorption layer in the inner layer of the urine and feces collection bag is an absorption layer compounded by polymer absorbent resin and fluff fiber. The inner layer and the outer layer of the urine and feces collection bag are integrated.

According to the disposable nursing device with the urine and feces back-leakage prevention collection function above, cross sections of the bag opening, a bag bottom and a bag body of the urine and feces collection bag are all round or oval when the urine and feces collection bag is unfolded; the bag opening of the urine and feces collection bag is connected with the connecting port on the nursing pants body through the catch tray, the urine and feces collection bag connected with a front side of the nursing pants body is a first urine and feces collection bag with a diameter of a bag opening smaller than a diameter of a bag bottom; and the urine and feces collection bag connected with a rear side of the nursing pants body is a second urine and feces collection bag with a diameter of a bag opening equal to a diameter of a bag bottom, and a backflow prevention ring is arranged below the bag opening in the second urine and feces collection bag, which is preferably made of flexible plastic sheet to avoid backflow of wastes in the bag. When a man uses the disposable nursing device, the two urine and feces collection bags are respectively adhered to corresponding positions of the nursing pants body of the male style, when a woman uses the disposable nursing device, the second urine and feces collection bag is adhered to the corresponding position of the nursing pants body of the female type, and then the paper diaper can be worn.

According to the disposable nursing device with the urine and feces back-leakage prevention collection function above, the catch tray is circular, a back surface of the catch tray is connected and fixed with the bag opening of the urine and feces collection bag through sewing, the urine and feces collection opening at the middle of the catch tray is communicated with the bag opening of the urine and feces collection bag, a diameter of the urine and feces collection opening is smaller than a diameter of the bag opening of the urine and feces collection bag, a diameter of the catch tray is greater than a diameter of the connecting port on the nursing pants body, the catch tray is arranged on an inner surface of the nursing pants body in the connecting port, and a bag body of the urine and feces collection bag extends out of the nursing pants body through the connecting port.

According to the disposable nursing device with the urine and feces back-leakage prevention collection function above, an acute angle is formed between the bag body of the urine and feces collection bag and the catch tray, so that the bag body of the urine and feces collection bag extends out of the connecting port of the nursing pants body and then inclines to the bottom portion of the nursing pants body, and a raised reinforcing line is arranged on a surface of a joint of the urine and feces collection bag and the catch tray facing an outside of the urine and feces collection bag along a length direction of the urine and feces collection bag, so that the bag body of the urine and feces collection bag is tightened to form an acute angle with the catch tray.

According to the disposable nursing device with the urine and feces back-leakage prevention and collection functions above, the catch tray is provided with an adhering area outside a fixed position between the back surface of the catch tray and the bag opening of the urine and feces collection bag, and the adhering area is corresponding to and connected with an adhesive strip at an edge of the connecting port on the nursing pants body.

According to the disposable nursing device with the urine and feces back-leakage prevention collection function above, two surfaces of the catch tray are respectively a soft non-woven fabric layer, a soft plastic film layer is sandwiched between the two soft non-woven fabric layers, the three layers are fixed into a whole, the back surface of the catch tray faces the inner surface of the nursing pants body and is provided with the adhering area on the back surface of the catch tray, and transparent adhesive dressing is arranged on the adhering area. The soft non-woven fabric layer and the soft plastic film layer are integrated. The adhesive dressing at the adhering area is a polymer elastomer, which is soft, transparent and breathable, and does not damage the skin of the user. Except for the adhering area, the catch tray is also provided with an adhesive dressing free area for convenient disassembly and replacement, so as to prevent an external force from damaging the urine and feces collection bag to pollute hands of medical personnel during disassembly; and a surface of the catch tray is provided with an annular scale, and according to specific conditions, the urine and feces collection opening can be cut in the middle according to the scale of the catch tray to adjust the urine and feces collection opening into a required size to meet the needs of the user.

The disposable nursing device with the urine and feces back-leakage prevention collection function provided by the present invention has the following advantages.

The present invention can be widely applied to the collection of normal defecating (including urine and feces) of long-term bedridden disabled elderly, patients, children and pets, and can be specifically applied to patients suffering a surgery, disabled elderly, paralyzed patients, caesarean patients, physically inconvenienced people, unconscious patients, vegetative patients, disabled patients, long-term bedridden patients, enuresis patients, continuously transfused patients, walking enuresis patients, children, pets, emergencies on highway, and the like.

According to the present invention, in order to really realize rapid urine absorption, reduction of a polluted area after defecation, and reduction of a contact area with skin after defecating to a special device, a backflow prevention port is added in the design to prevent a soft excrement from flowing backwards due to different sleeping postures of a user, and the possibility of bedsore and ulceration of the skin caused by pollutants is greatly reduced due to the use of a polymer water absorption material.

For a nurse worker, when the detachable product of the present invention is used, the adhering area only needs to be adhered to a position of a corresponding hole in the paper diaper, and the urine and feces defecated by the disabled elderly (sick) at a fixed position enter the corresponding urine and feces collection bag, and are processed to a designated place, thus greatly reducing a working intensity. If the patient defecates, only one feces bag needs to be replaced, if the patent defecates many times a day, the bag can be replaced by turning the patient to the left side and to the right side, thus greatly reducing the working intensity of the worker, and having economy and low cost. The present invention really benefits both the bedridden (sick) and nursing people. The personal dignity of the user is also guaranteed. In addition, the catch tray is provided with the diameter scale, and according to specific conditions, the urine and feces collection opening can be adjusted to a required size to meet the needs of the user through cutting according to the scale of the catch tray; the adhesive dressing at the adhering position is the polymer elastomer, which is soft, transparent and breathable, and does not damage the skin of the user; and the catch tray is also provided with the adhesive dressing free area for convenient disassembly and replacement, so as to prevent an external force from damaging the urine and feces collection bag to pollute hands of medical personnel during disassembly.

DESCRIPTION OF THE EMBODIMENTS

The detained embodiments of the present invention are further described hereinafter with reference to the drawings.

Figure 1:
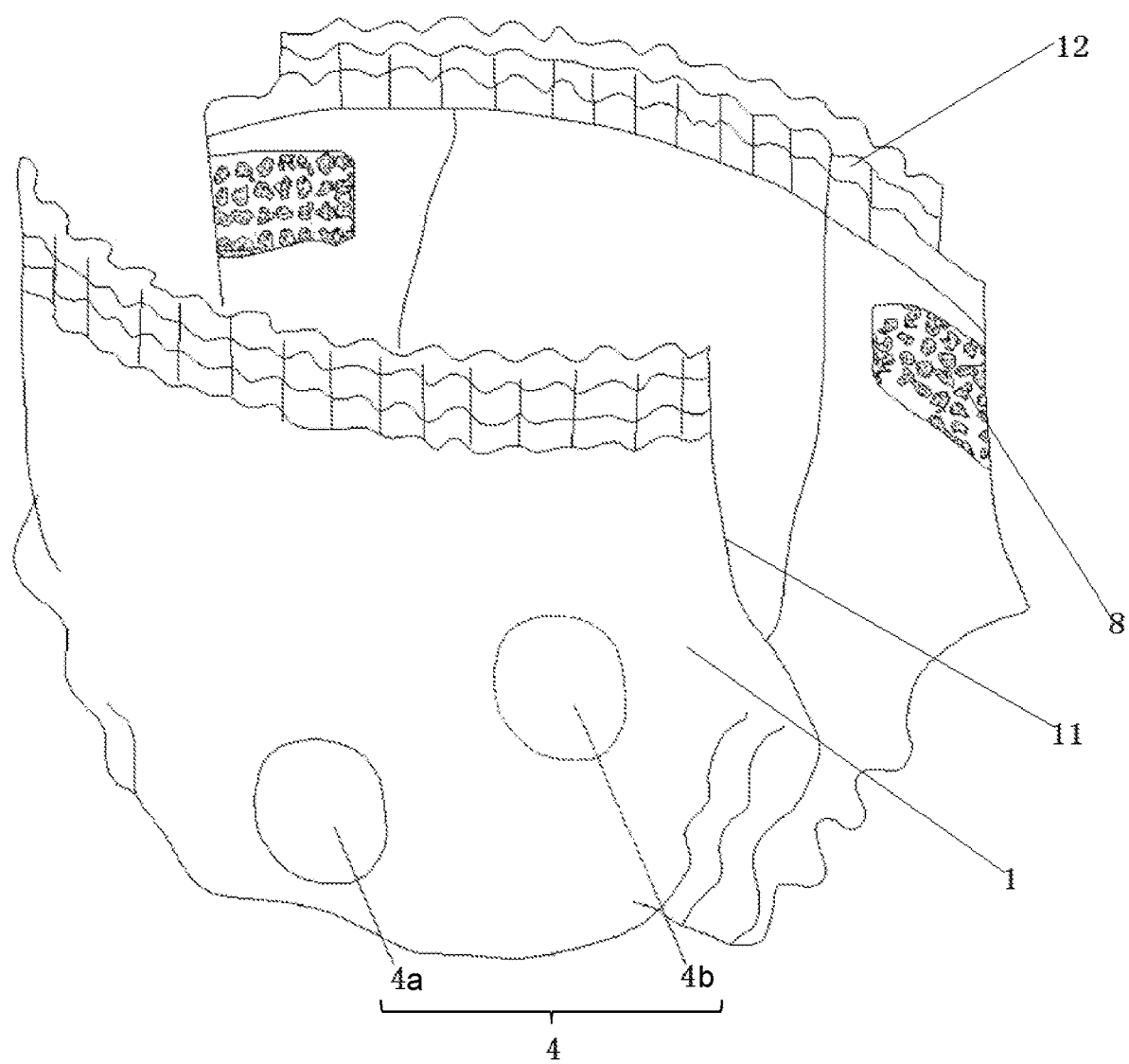
FIG. 1 is a diagram of a nursing pants body of the present invention.
Figure 2:
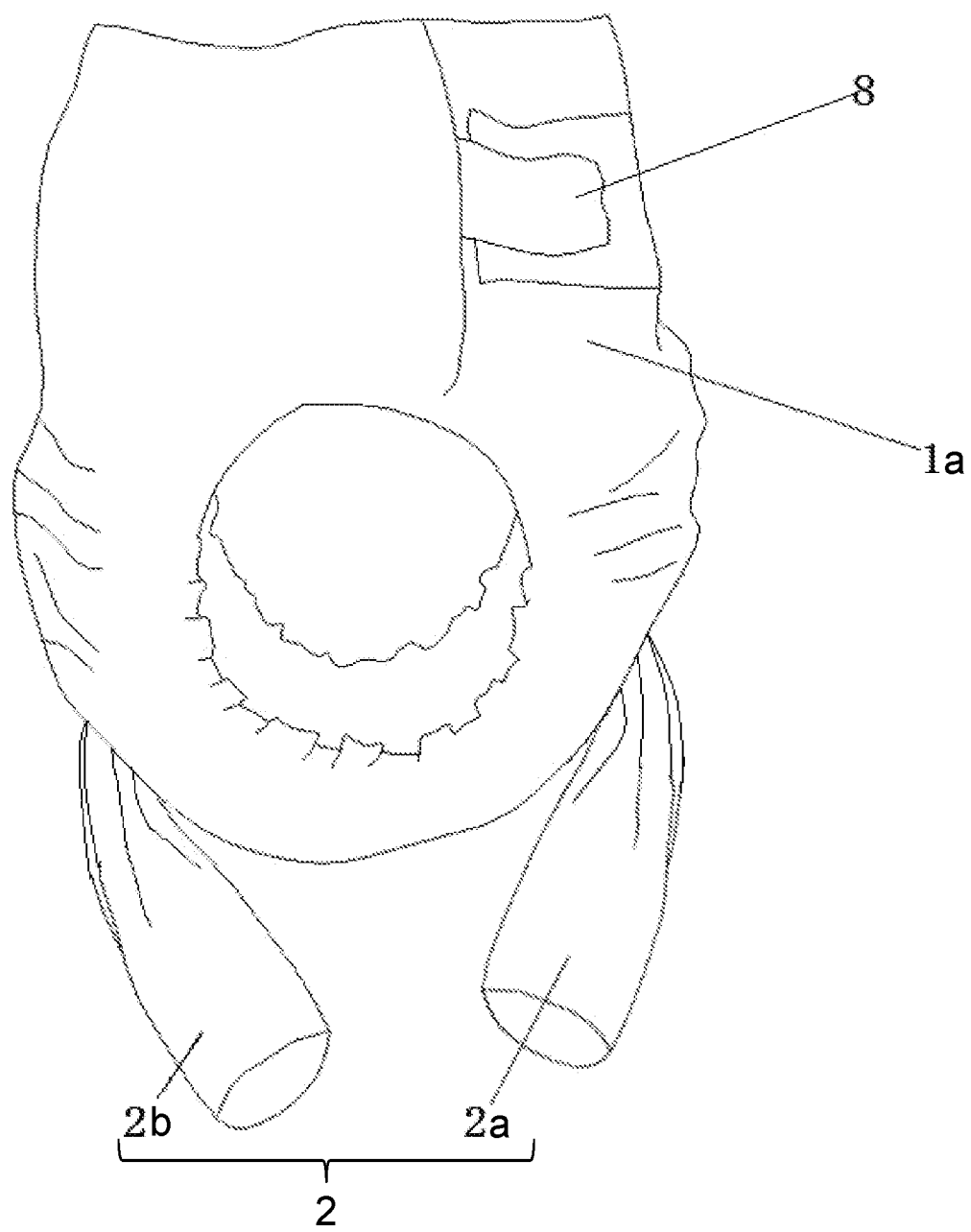
FIG. 2 is a diagram of nursing pants of a male style.
Figure 3:
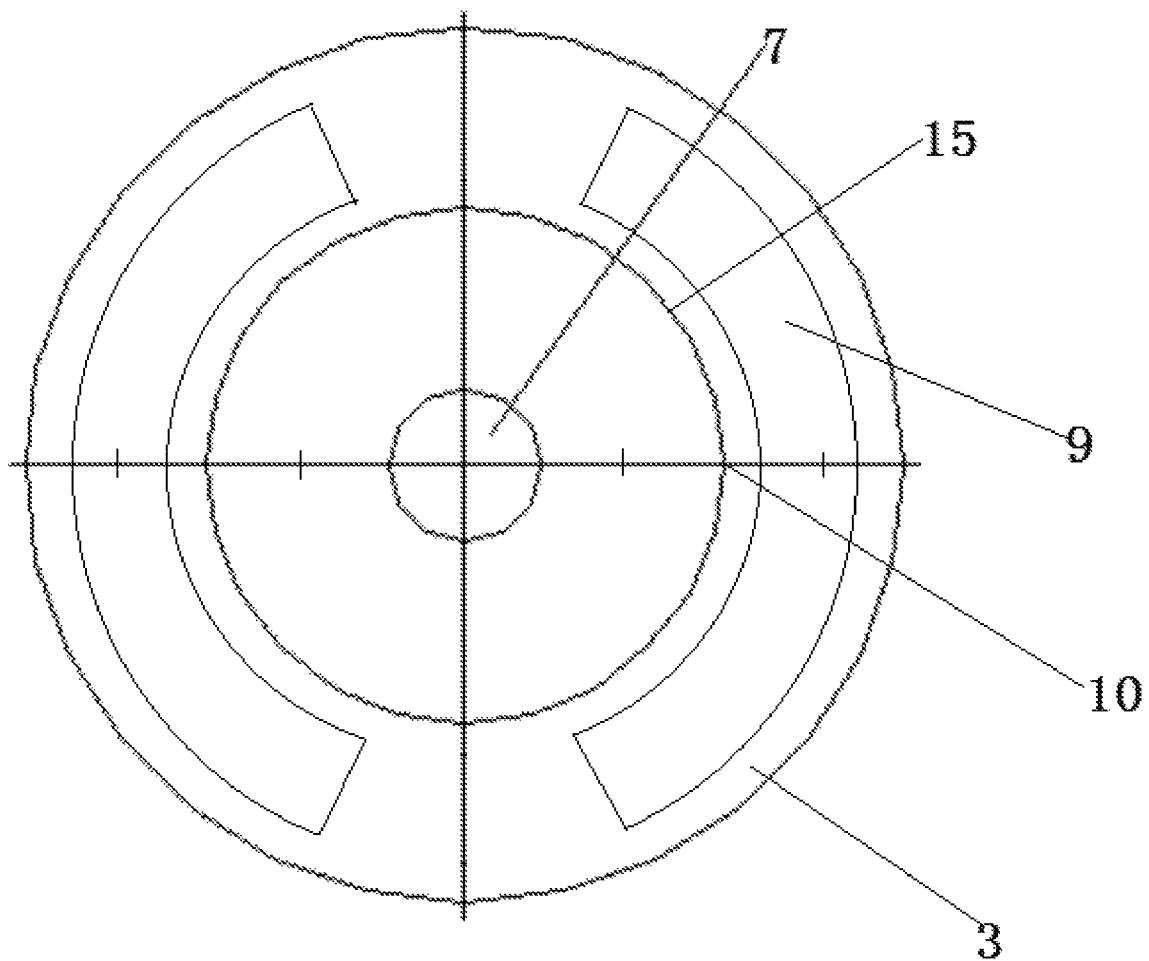
FIG. 3 is a diagram of a catch tray of the present invention.
Figure 4:
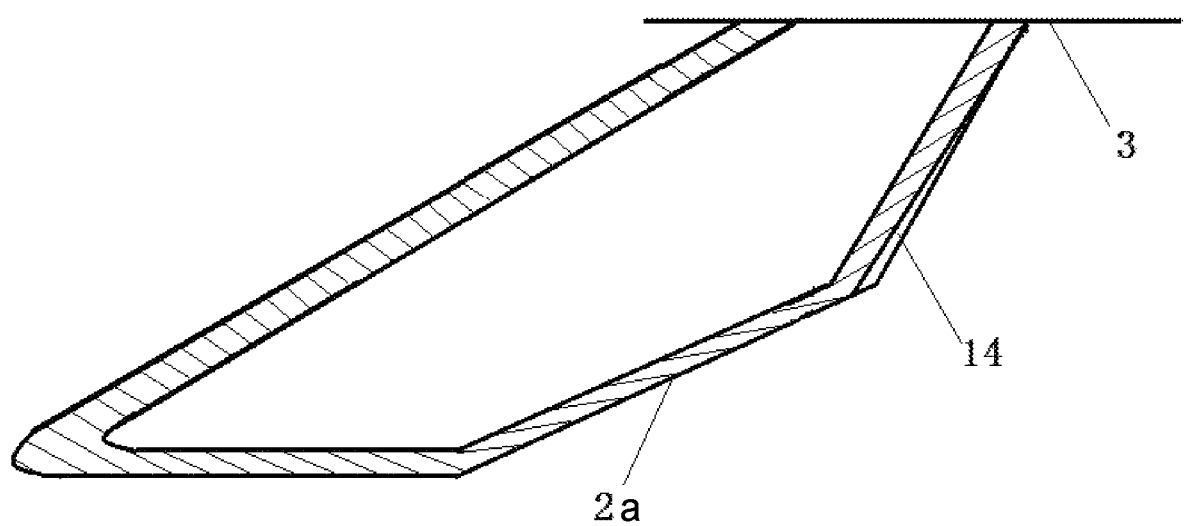
FIG. 4 is a diagram of a first urine and feces collection bag on a front side of the present invention.
Figure 5:
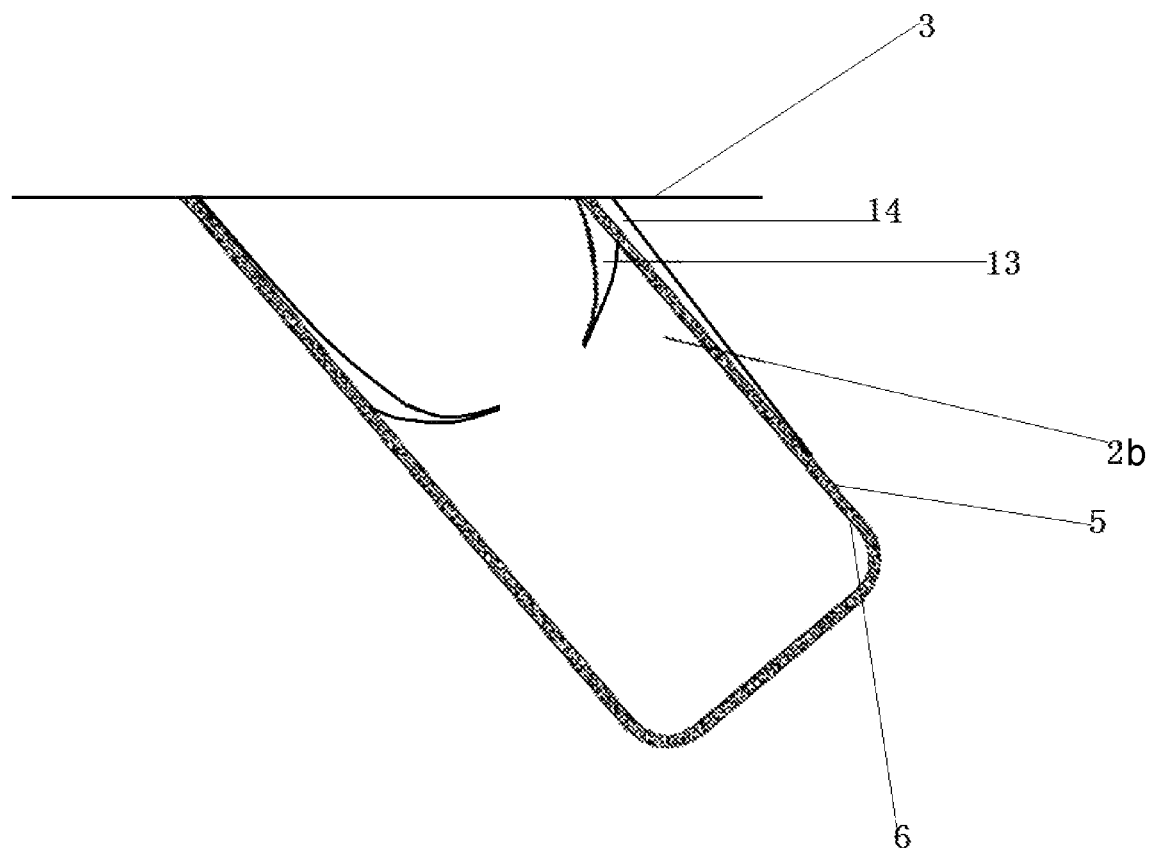
FIG. 5 is a diagram of a second urine and feces collection bag on a rear side of the present invention.
Figure 6:
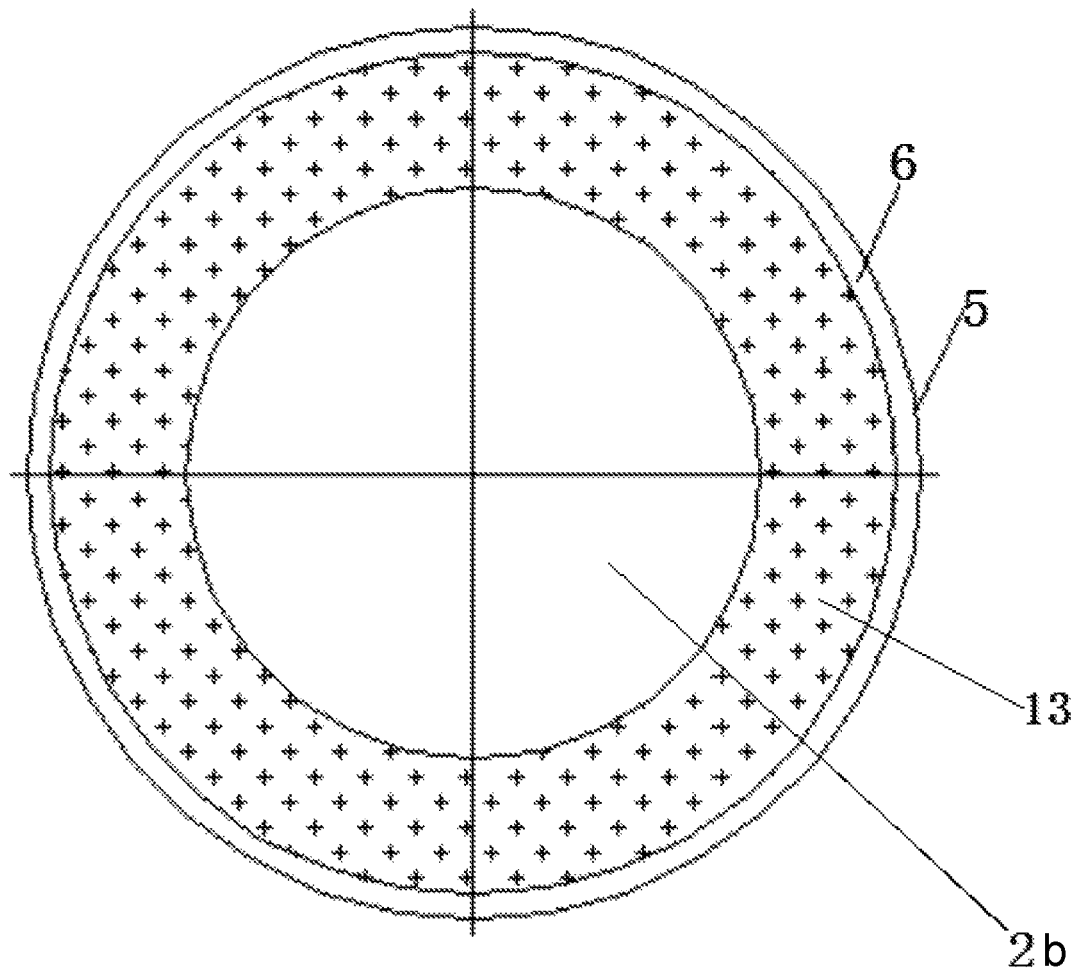
FIG. 6 is a cross section view of the second urine and feces collection bag on the rear side of the present invention.
Figure 7:
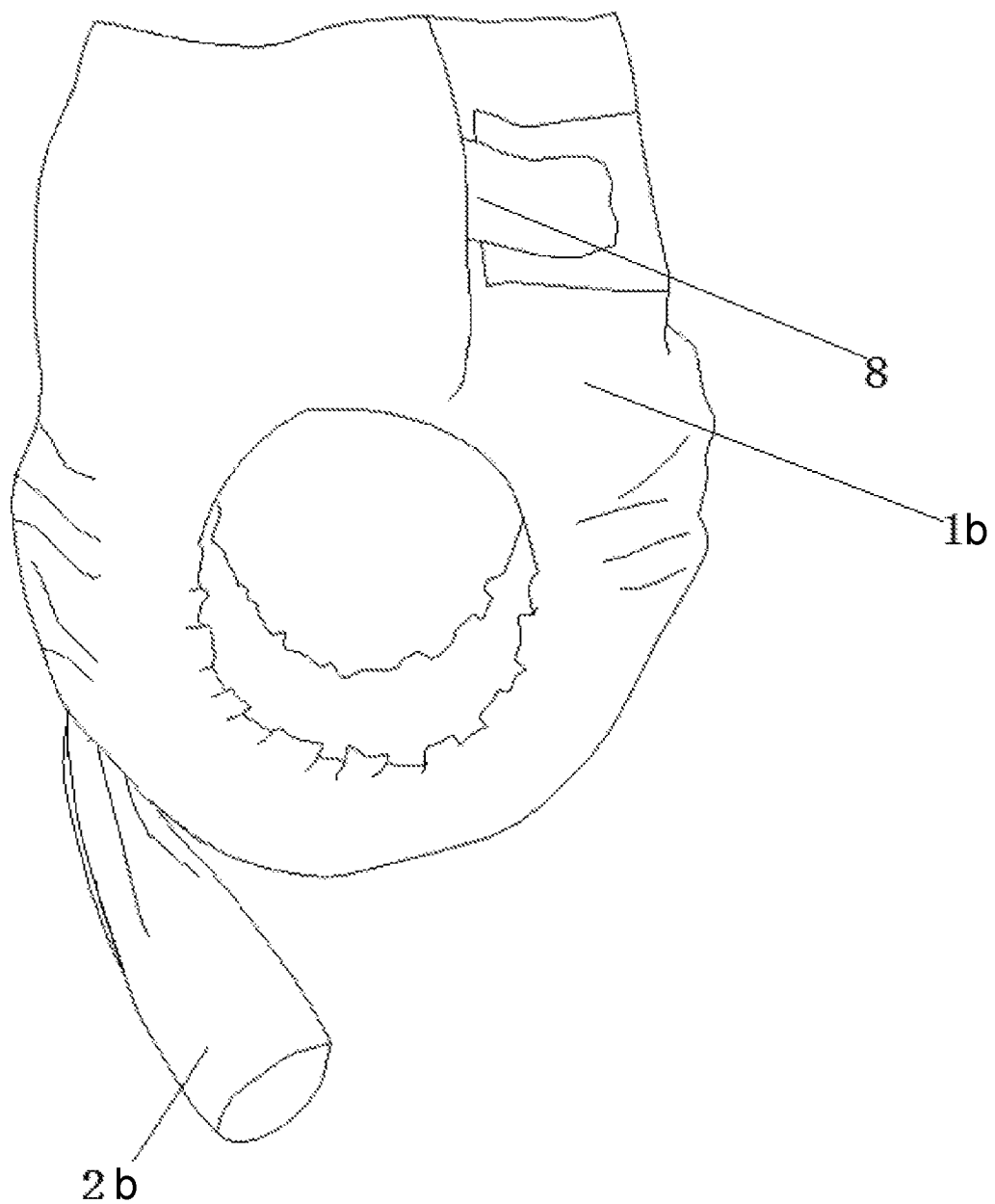
FIG. 7 is a diagram of nursing pants of a female style.

As shown in FIGS. 1 to 7, a disposable nursing device with a urine and feces back-leakage prevention collection function provided by the present invention includes a nursing pants body 1, a urine and feces collection bag 2 and a catch tray 3; the nursing pants body 1 is a paper diaper which can be opened and closed on left and right sides, and the nursing pants body 1 is provided with a connecting port 4; the urine and feces collection bag 2 is provided with an outer layer 5 and an inner layer 6, the outer layer 5 is a soft non-woven fabric, and the inner layer 6 is a polymer absorption layer; a bottom portion of the urine and feces collection bag 2 is closed, and a top portion of the urine and feces collection bag 2 is provided with a bag opening; and a urine and feces collection opening 7 is arranged at a middle of the catch tray 3, and one side of the catch tray 3 is connected with the bag opening of the urine and feces collection bag 2 and is connected with the connecting port 4 on the nursing pants body 1.

The left and right sides of the nursing pants body 1 are respectively provided with an opening 11 penetrating from top to bottom, and surfaces of the nursing pants body 1 on two sides of the openings 11 are respectively provided with a corresponding adhesive tape 8.

The nursing pants body 1 includes a male style and a female style, the nursing pants body of the male style 1a is respectively provided with one connecting port 4 at a front side and a rear side, the nursing pants body of the female style 1b is provided with one connecting port 4 at a rear side, the connecting port 4 is a circular port corresponding to a defecation position of a human body, and an inner surface of the nursing pants body 1 at an edge of the connecting port 4 is provided with an adhesive strip.

An outer surface of the nursing pants body 1 is a soft non-woven fabric, an inner surface of the nursing pants body 1 is a polymer absorption layer, and the polymer absorption layer is an absorption layer compounded by polymer absorbent resin and fluff fiber.

The polymer absorption layer in the inner layer 6 of the urine and feces collection bag 2 is an absorption layer compounded by polymer absorbent resin and fluff fiber.

Cross sections of the bag opening, a bag bottom and a bag body of the urine and feces collection bag 2 are all round or oval when the urine and feces collection bag 2 is unfolded; the bag opening of the urine and feces collection bag 2 is connected with the connecting port 4 on the nursing pants body 1 through the catch tray 3, the urine and feces collection bag 2 connected with a front side of the nursing pants body 1 is a first urine and feces collection bag 2a with a diameter of a bag opening smaller than a diameter of a bag bottom; and the urine and feces collection bag 2 connected with a rear side of the nursing pants body 1 is a second urine and feces collection bag 2b with a diameter of a bag opening equal to a diameter of a bag bottom, and a backflow prevention ring 13 is arranged below the bag opening in the second urine and feces collection bag 2b.

The catch tray 3 is circular, a back surface of the catch tray 3 is connected and fixed with the bag opening of the urine and feces collection bag 2 through sewing, the urine and feces collection opening 7 at the middle of the catch tray 3 is communicated with the bag opening of the urine and feces collection bag 2, a diameter of the catch tray 3 is greater than a diameter of the connecting port 4 on the nursing pants body 1, the catch tray 3 is arranged in the connecting port 4, and a bag body of the urine and feces collection bag 2 extends out of the nursing pants body 1 through the connecting port 4.

An acute angle is formed between the bag body of the urine and feces collection bag 2 and the catch tray 3, so that the bag body of the urine and feces collection bag 2 extends out of the connecting port 4 of the nursing pants body 1 and then inclines to the bottom portion of the nursing pants body 1, and a raised reinforcing line 14 is arranged on a surface of a joint of the urine and feces collection bag 2 and the catch tray 3 facing an outside of the urine and feces collection bag 2 along a length direction of the urine and feces collection bag 2.

The catch tray 3 is provided with an adhering area 9 outside a fixed position 15 between the back surface of the catch tray 3 and the bag opening of the urine and feces collection bag 2, and the adhering area 9 is corresponding to and connected with an adhesive strip at an edge of the connecting port 4 on the nursing pants body 1.

Two surfaces of the catch tray 3 are respectively a soft non-woven fabric layer, and a soft plastic film layer is sandwiched between the two soft non-woven fabric layers; and the back surface of the catch tray 3 faces the inner surface of the nursing pants body 1 and is provided with the adhering area 9, and transparent adhesive dressing is arranged on the adhering area 9.

A surface of the catch tray 3 is provided with an annular scale 10.

The disposable nursing device with a urine and feces back-leakage prevention collection function is further described hereinafter with reference to the embodiment.

First Embodiment

A disposable nursing device with a urine and feces back-leakage prevention collection function includes a nursing pants body 1, a urine and feces collection bag 2, and a catch tray 3. The nursing pants are disposable sanitary articles after sterilization treatment.

The nursing pants body 1 is a paper diaper which can be opened and closed on left and right sides, and the nursing pants body 1 is provided with a connecting port 4. The left and right sides of the nursing pants body 1 are respectively provided with an opening 11 penetrating from top to bottom, so that the nursing pants body 1 can be unfolded into a plane; and surfaces of the nursing pants body 1 on two sides of the openings 11 are respectively provided with a corresponding adhesive tape 8. The adhesive tape 8 is preferably in the form of an adhesive sheet or a hook and loop, and can be repeatedly opened and closed many times. An upper edge of the nursing pants body 1 is provided with an elastic edge 12 with elasticity. The nursing pants body 1 includes a male style and a female style, the nursing pants body of the male style 1a is respectively provided with one connecting port 4 at a front side and a rear side, the nursing pants body of the female style 1b is provided with one connecting port 4 at a rear side, the connecting port 4 is a circular port corresponding to a defecation position of a human body, and an inner surface of the nursing pants body 1 at an edge of the connecting port 4 is provided with an adhesive strip. An outer surface of the nursing pants body 1 is a soft non-woven fabric, an inner surface of the nursing pants body 1 is a polymer absorption layer, and the polymer absorption layer is an absorption layer compounded by polymer absorbent resin and fluff fiber. The soft non-woven fabric and the polymer absorption layer are integrated.

The urine and feces collection bag 2 is provided with an outer layer 5 and an inner layer 6, the outer layer is 5 a soft non-woven fabric, and the inner layer 6 is a polymer absorption layer; and a bottom portion of the urine and feces collection bag 2 is closed, a top portion of the urine and feces collection bag 2 is provided with a bag opening, and a bag body is a closed structure except at the bag opening. The polymer absorption layer in the inner layer 6 of the urine and feces collection bag 2 is an absorption layer compounded by polymer absorbent resin and fluff fiber. The inner layer 6 and the outer layer 5 of the urine and feces collection bag 2 are integrated. Cross sections of the bag opening, a bag bottom and a bag body of the urine and feces collection bag 2 are all round or oval when the urine and feces collection bag 2 is unfolded; the bag opening of the urine and feces collection bag 2 is connected with the connecting port 4 on the nursing pants body 1 through the catch tray 3, the urine and feces collection bag 2 connected with a first connecting port 4a at a front side of the nursing pants body 1 is a first urine and feces collection bag 2a with a diameter of a bag opening smaller than a diameter of a bag bottom; and the urine and feces collection bag 2 connected with a second connecting port 4b at a rear side of the nursing pants body 1 is a second urine and feces collection bag 2b with a diameter of a bag opening equal to a diameter of a bag bottom, and a backflow prevention ring 13 is arranged below the bag opening in the second urine and feces collection bag 2b, which is preferably made of flexible plastic sheet to avoid backflow of wastes in the bag. When a man uses the disposable nursing device, the two urine and feces collection bags 2 are respectively adhered to corresponding positions of the nursing pants body of the male style 1a, when a woman uses the disposable nursing device, the second urine and feces collection bag 2b is adhere to the corresponding position of the nursing pants body of the female type 1b, and then the paper diaper can be worn.

A urine and feces collection opening 7 is arranged at a middle of the catch tray 3, and one side of the catch tray 3 is connected with the bag opening of the urine and feces collection bag 2 and is connected with the connecting port 4 on the nursing pants body 1. The catch tray 3 is circular, a back surface of the catch tray 3 is connected and fixed with the bag opening of the urine and feces collection bag 2 through sewing, the urine and feces collection opening 7 at the middle of the catch tray 3 is communicated with the bag opening of the urine and feces collection bag 2, and a diameter of the urine and feces collection opening is smaller than a diameter of the bag opening of the urine and feces collection bag. A diameter of the catch tray 3 is greater than a diameter of the connecting port 4 on the nursing pants body 1, the catch tray 3 is arranged on an inner surface of the nursing pants body 1 in the connecting port 4, and the bag body of the urine and feces collection bag 2 passes through the connecting port 4 on the nursing pants body 1, and extends out of the nursing pants body 1 through the connecting port 4. An acute angle is formed between the bag body of the urine and feces collection bag 2 and the catch tray 3, so that the bag body of the urine and feces collection bag 2 extends out of the connecting port 4 of the nursing pants body 1 and then inclines to the bottom portion of the nursing pants body 1, and a raised reinforcing line 14 is arranged on a surface of a joint of the urine and feces collection bag 2 and the catch tray 3 facing an outside of the urine and feces collection bag 2 along a length direction of the urine and feces collection bag 2, so that the bag body of the urine and feces collection bag 2 is tightened to form an acute angle with the catch tray 3.

The catch tray 3 is provided with an adhering area 9 outside a fixed position 15 between the back surface of the catch tray 3 and the bag opening of the urine and feces collection bag 2, and the adhering area 9 is corresponding to and connected with an adhesive strip at an edge of the connecting port 4 on the nursing pants body 1. Two surfaces of the catch tray 3 are respectively a soft non-woven fabric layer, a soft plastic film layer is sandwiched between the two soft non-woven fabric layers, the three layers are fixed into a whole, the back surface of the catch tray 3 faces the inner surface of the nursing pants body 1 and is provided with the adhering area 9 on the back surface of the catch tray 3, and transparent adhesive dressing is arranged on the adhering area 9. The soft non-woven fabric layer and the soft plastic film layer are integrated. The adhesive dressing at the adhering area 9 is a polymer elastomer, which is soft, transparent and breathable, and does not damage the skin of the user. Except for the adhering area 9, the catch tray 3 is also provided with an adhesive dressing free area for convenient disassembly and replacement, so as to prevent an external force from damaging the urine and feces collection bag 2 to pollute hands of medical personnel during disassembly. A surface of the catch tray 3 is provided with an annular scale 10, and according to specific conditions, the urine and feces collection opening 7 can be cut in the middle according to the scale of the catch tray 3 to adjust the urine and feces collection opening 7 into a required size to meet the needs of the user.

The disposable nursing device with the urine and feces back-leakage prevention collection function provided by the present invention improves the defect of no urine and feces collection device in a wearing process of the paper diapers of the male type and the female type, and provides a direct defecating device with reasonable structure and convenient use. A device for preventing the urine and feces from flowing back is use in the urine and feces collection bag, and the middle layer is provided with the polymer hygroscopic material, so that the water in the urine and feces of the user can be quickly absorbed in straight sleeping posture and left-side and right-side sleeping posture, so as to dry the urine and feces. The skin pollution area is greatly reduced. Immediate replacement avoids skin irritation, effectively prevents the occurrence of clinical complications, reduces nursing burden and improves the quality of life of the patient.

Although the contents of the present invention have been described in detail in the preferred embodiment above, it should be recognized that the description above should not be deemed as a limitation of the present invention. Various modifications and substitutions of the present invention made by those skilled in the art after reading the contents above to the present invention will be apparent. Therefore, the protection scope of the present invention should be defined by the appended claims.

What is claimed is:

1. A disposable nursing device with a urine and feces back-leakage prevention collection function, comprising a nursing pants body, a urine and feces collection bag, and a catch tray, wherein the nursing pants body is a paper diaper which can be opened and closed on left and right sides, and the nursing pants body is provided with a connecting port;

the urine and feces collection bag is provided with an outer layer and an inner layer, the outer layer is a soft non-woven fabric, and the inner layer is a polymer absorption layer; a bottom portion of the urine and feces collection bag is closed, and a top portion of the urine and feces collection bag is provided with a bag opening; and a urine and feces collection opening is arranged at a middle of the catch tray, and one side of the catch tray is connected with the bag opening of the urine and feces collection bag, and is connected with the connecting port on the nursing pants body, wherein the catch tray is circular, a back surface of the catch tray is connected and fixed with the bag opening of the urine and feces collection bag through sewing, the urine and feces collection opening at the middle of the catch tray is communicated with the bag opening of the urine and feces collection bag, a diameter of the catch tray is greater than a diameter of the connecting port on the nursing pants body, the catch tray is arranged in the connecting port, and a bag body of the urine and feces collection bag extends out of the nursing pants body through the connecting port;

an acute angle is formed between the bag body of the urine and feces collection bag and the catch tray, so that the bag body of the urine and feces collection bag extends out of the connecting port of the nursing pants body and then inclines to the bottom portion of the nursing pants body, and a raised reinforcing line is arranged on a surface of a joint between the urine and feces collection bag and the catch tray, wherein the joint faces an outside of the urine and feces collection bag along a length direction of the urine and feces collection bag.

2. The disposable nursing device with the urine and feces back-leakage prevention collection function according to claim 1, wherein the left and right sides of the nursing pants body are respectively provided with an opening penetrating from top to bottom, so that the nursing pants body can be unfolded into a plane, and surfaces of the nursing pants body on two sides of the openings are respectively provided with a corresponding adhesive tape.

3. The disposable nursing device with the urine and feces back-leakage prevention collection function according to claim 2, wherein the nursing pants body comprises a male style or a female style, the nursing pants body of the male style is respectively provided with one connecting port at a front side and a rear side, the nursing pants body of the female style is provided with one connecting port at a rear side, the connecting port is a circular port corresponding to a defecation position of a human body.

4. The disposable nursing device with the urine and feces back-leakage prevention collection function according to claim 3, wherein an outer surface of the nursing pants body is a soft non-woven fabric, an inner surface of the nursing pants body is a polymer absorption layer, and the polymer absorption layer is an absorption layer compounded by polymer absorbent resin and fluff fiber.

5. The disposable nursing device with the urine and feces back-leakage prevention collection function according to claim 1, wherein the polymer absorption layer in the inner layer of the urine and feces collection bag is an absorption layer compounded by polymer absorbent resin and fluff fiber.

6. The disposable nursing device with the urine and feces back-leakage prevention collection function according to claim 5, wherein cross sections of the bag opening, a bag bottom and a bag body of the urine and feces collection bag are all round or oval when the urine and feces collection bag is unfolded; the bag opening of the urine and feces collection bag is connected with the connecting port on the nursing pants body through the catch tray, the urine and feces collection bag connected with a front side of the nursing pants body is a first urine, the first urine feces collection bag and has a first bag opening and a first bag bottom, a diameter of the first bag opening smaller than a diameter of the first bag bottom; and the urine and feces collection bag connected with a rear side of the nursing pants body is a second urine, the second urine feces collection bag and has a second bag opening and a second bag bottom, a diameter of the second bag opening equal to a diameter of the second bag bottom, and a backflow prevention ring is arranged below the bag opening in the second urine and feces collection bag.

7. The disposable nursing device with the urine and feces back-leakage prevention collection function according to claim 1, wherein the catch tray is provided with an adhering area outside a fixed position between the back surface of the catch tray and the bag opening of the urine and feces collection bag, and the adhering area is corresponding to and connected with an adhesive strip at an edge of the connecting port on the nursing pants body.

8. The disposable nursing device with the urine and feces back-leakage prevention collection function according to claim 7, wherein the catch tray comprises two soft non-woven fabric layers and a soft plastic film layer sandwiched between the two soft non-woven fabric layers; and the back surface of the catch tray faces the inner surface of the nursing pants body and is provided with the adhering area, and transparent adhesive dressing is arranged on the adhering area; and a surface of the catch tray is provided with an annular scale.

* * * * *